Figure 1:
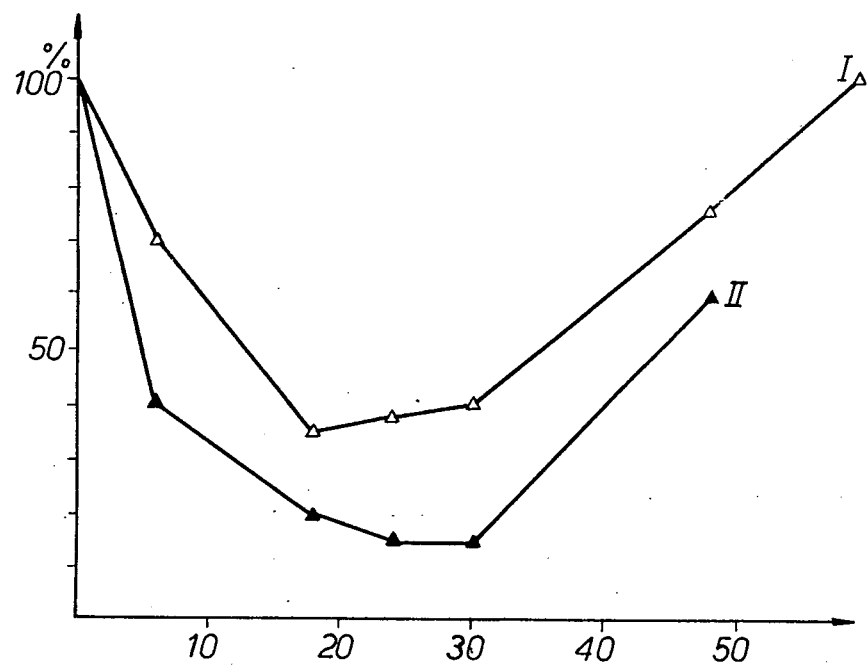

United States Patent [19]

Mardiguian

[11] 3,957,879
[45] May 18, 1976

[54] INDANE-1,3-DIONE DERIVATIVES
[75] Inventor: Jean Mardiguian, Saint-Maur, France
[73] Assignee: Societe d'Etude et d'Eploitation de Marques Mar-Pha, France
[22] Filed: Sept. 9, 1974
[21] Appl. No.: 504,543

[30] Foreign Application Priority Data
Sept. 12, 1973 United Kingdom............ 42904/73

[52] U.S. Cl............................ 260/590 FA; 424/331
[51] Int. Cl.²........................................ C07C 49/76
[58] Field of Search .............. 260/590 FA; 424/331

[56] References Cited
UNITED STATES PATENTS
| | | | |
|---|---|---|---|
| 2,310,949 | 2/1943 | Ford et al. .................... | 260/590 FA |
| 2,842,596 | 7/1958 | Freedman et al............. | 260/590 FA |
| 2,884,357 | 4/1959 | Hazleton et al. ............. | 260/590 FA |
| 3,153,612 | 10/1964 | Molho et al. ................. | 260/590 FA |

OTHER PUBLICATIONS
Ohno, Chem. Abst., Vol. 80, 145895g (1974).

Primary Examiner—James O. Thomas, Jr.
Assistant Examiner—James H. Reamer
Attorney, Agent, or Firm—Marn & Jangarathis

[57] ABSTRACT

The invention provides compounds of formula:

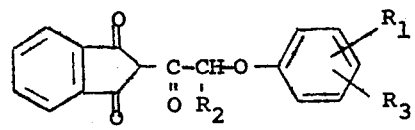

wherein each of the groups $R_1$ and $R_2$, which may be the same or different, is a hydrogen atom or an alkyl group having 1 to 3 carbon atoms and $R_3$ is a hydrogen or halogen atom, an alkyl group having 1 to 3 carbon atoms or a methoxy, trifluoromethyl or nitro group.

The compounds are useful for inducing hypothrombinaemia.

13 Claims, 15 Drawing Figures

INDANE-1,3-DIONE DERIVATIVES

The present invention relates to new compounds which are indane-1,3-dione derivatives, to a process for preparing them and to pharmaceutical compositions containing them.

The compounds have the general formula (I)

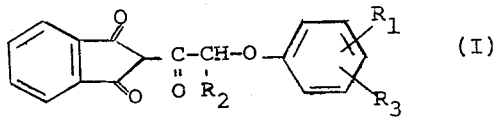

wherein each of $R_1$ and $R_2$, which may be the same or different is a hydrogen atom or a lower alkyl group having 1 to 3 carbon atoms, and $R_3$ is a hydrogen or halogen atom, a lower alkyl radical having 1 to 3 carbon atoms, or a methoxy, trifluoromethyl or nitro group.

The compounds of the invention can be prepared by acylating indane-1,3-dione of general formula (II) with an aryloxy-alkanoic acid chloride of general formula (III) according to the equation:

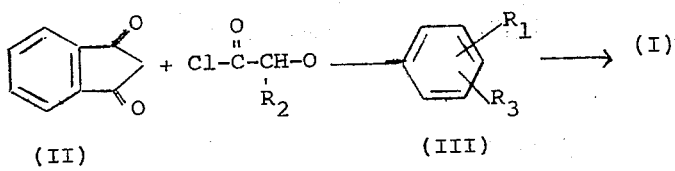

wherein $R_1$, $R_2$ and $R_3$ are as defined above. The acylation reaction can be performed in pyridine, in the presence of a few drops of piperidine. It is also possible to carry out the reaction starting from the sodium salt of the indane-1,3-dione in a solvent such as benzene, tetrahydrofuran, monoglyme or diglyme.

It is also possible to prepare the compounds of the invention by condensing a compound of general formula (IV)

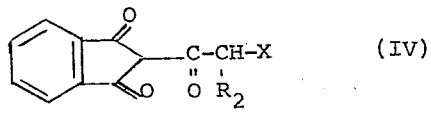

wherein $R_2$ is as defined above and X is a halogen atom, with a sodium phenate of general formula (V)

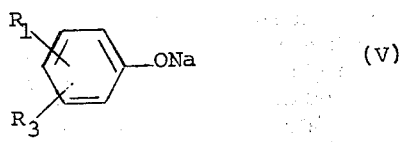

wherein $R_1$ and $R_3$ are as defined above, in an organic solvent.

The compounds of the invention possess a powerful hypothrombinaemia-inducing activity which has been demonstrated in rats and rabbits. They can be used as anti-coagulants.

The invention therefore also provides pharmaceutical compositions comprising a compound of general formula (I) and a pharmaceutically acceptable carrier or diluent.

The invention is illustrated by the following Examples, wherein the infrared spectra (IR) are measured in 0.1 mol/l solutions in chloroform ($CHCl_3$) or in a 3% dispersion in potassium bromide (KBr); the wavelength of the most intense characteristic bands are given. The nuclear magnetic resonance spectra are measured in 0.2 mol/l solutions in deuterated chloroform and the results relative to trimethylsilane are given.

EXAMPLE 1

14.6 G (0.1 mol) of indane-1,3-dione in 300 ml of benzene is added to a suspension of 5.4 g (0.1 mol) of sodium methylate in 30 ml of dry benzene. The mixture is stirred for 10 minutes at ambient temperature and 32.8 g (0.15 mol) of freshly distilled 2-(4'-chlorophenoxy)-isopropionic acid chloride in 50 ml of benzene are slowly introduced.

The solution is refluxed for 4 hours and then allowed to cool and poured into 10% hydrochloric acid. The organic phase is decanted, washed with water and dried over sodium sulphate. The solvent is evapoated in vacuo. The residue is taken up in 200 ml of ethanol. The solid which separates out is crystallised twice from ethyl acetate to give 5 g of a yellow product which is 2-[2'-(4''-chlorophenoxy)isopropionyl)]indane-1,3-dione, melting point = 170°C. Empirical formula: $C_{18}H_{13}ClO_4$. Molecular weight: 328.5. Elementary analysis:

| | C | H | Cl |
|---|---|---|---|
| Calculated % | 65.75 | 3.98 | 10.77 |
| Found % | 65.62 | 3.93 | 10.74 |

IR($CHCl_3$): 1,710 cm$^{-1}$ nonchelated C = O; 1,660 chelated C = O; 1,610 C = C; 1,595 ortho-disubstituted aromatic ring; 1,490 para-disubstituted aromatic ring; 1220 ether bond.

| NMR: | $CH_3$ | 1.75 | ppm | doublet; |
|---|---|---|---|---|
| | CH | 6.1 | ppm | quadruplet; |
| |  | 7.05 | ppm | quadruplet; |
| |  | 7.8 | ppm | singlet; |
| | OH | 11.8 | ppm | singlet. |

EXAMPLE 2

7.3 G (0.05 mol) of indane-1,3-dione in 150 ml of benzene is added to a suspension of 2.7 g (0.05 mol) of sodium methylate to 30 ml of dry benzene. The mixture is stirred for 10 minutes at ambient temperature and a solution of 13.1 g (0.05 mol) of freshly distilled 2-(4'-bromophenoxy)isopropionic acid chloride in 20 ml of benzene is introduced slowly.

The reaction mixture is refluxed for 4 hours and is poured into 10% aqueous hydrochloric acid. The organic phase is separated by decanting, washed with water and dried over sodium sulphate. After evaporating the solvent invacuo, the residue is taken up in 100 ml of ethanol. The precipitate which has formed is filtered off, washed with ethanol and recrystallised twice from ethyl acetate to give 2 g of a yellow product which is 2-[2'-(4''-bromophenoxy)isopropionyl]-indane-1,3-dione, melting point 163°C. Empirical formula: $C_{18}H_{13}O_4Br$. Molecular weight: 373. Elementary analysis:

| | C | H | Br |
|---|---|---|---|
| Calculated % | 57.90 | 3.49 | 21.45 |
| Found % | 58.03 | 3.76 | 21.35 |

IR(CHCl$_3$): 1,715 cm$^{-1}$ non-chelated C = O; 1,665 chelated C = O; 1,615 C = C; 1,595 and 1,490 disubstituted aromatic ring; 1,220 ether bond.

NMR:

| | | | |
|---|---|---|---|
| CH$_3$ | 1.65 | ppm | doublet; |
| CH | 6.05 | ppm | quadruplet; |
|  | 7.1 | ppm | quadruplet; |
|  | 7.75 | ppm | singlet; |
| OH | 12.5 | ppm | singlet; |

EXAMPLE 3

7.3 G (0.05 mol) of indane-1,3-dione in 150 ml of benzene is added to a suspension of 2.7 g (0.05 mol) of sodium methylate in 30 ml of dry benzene. The mixture is stirred for 10 minutes at ambient temperature and then 10.1 g (0.05 mol) of freshly distilled 2-(4'-fluorophenoxy)isopropionic acid chloride in 20 ml of benzene is introduced slowly. The reaction mixture is refluxed for 4 hours and then, after cooling, is poured into 10% aqueous hydrochloric acid. The organic phase is isolated by decanting, washed with water and dried over sodium sulphate. After evaporating the solvent in vacuo, the residue is taken up in 100 ml of ethanol. The precipitate which has formed is filtered off, washed with ethanol and recrystallised twice from ethyl acetate to give 2.4 g of a yellow product which is 2-[2'-(4''-fluorophenoxy)isopropionyl]indane-1,3-dione, melting point 136°C. Empirical formula: $C_{18}H_{13}O_4F$. Molecular weight: 312. Elementary analysis:

| | C | H | F |
|---|---|---|---|
| Calculated % | 69.23 | 4.17 | 6.09 |
| Found % | 69.2 | 4.29 | 5.95 |

IR(CHCl$_3$): 1,715 cm$^{-1}$ non-chelated C = O; 1,665 chelated C = O; 1,615 C = C; 1,510 and 1,600 disubstituted benzene ring; 1,220 ether bond.

NMR:

| | | | |
|---|---|---|---|
| CH$_3$ | 1.65 | ppm | doublet; |
| CH | 6.02 | ppm | quadruplet; |
|  | 6.85 | ppm | quadruplet; |
|  | 7.75 | ppm | singlet; |
| OH | 12.5 | ppm | singlet. |

EXAMPLE 4

2.6 G (0.024 mol) of para-cresol in 25 ml of toluene is added to a suspension of 2.5 g of sodium methylate in 25 ml of toluene. The mixture is stirred for 5 minutes and then 4.7 g (0.02 mol) of 2-(2'-chloropropionyl)-indane-1,3-dione dissolved in 50 ml of toluene and 20 ml of HMPT (hexamethylphosphotriamide) are introduced dropwise. The reaction mixture is refluxed for 17 hours and then after cooling, is poured into aqueous hydrochloric acid and the resulting mixture is extracted with benzene. After driving off the solvent, the residue is crystallised from isopropanol to give 4.95 g of pure 2-[2'-(4''-methylphenoxy) isopropionyl]indane-1,3-dione, melting point 104°C. Empirical formula: $C_{19}H_{16}O_4$; Molecular weight: 308.32; Elementary analysis:

| | C | H | O |
|---|---|---|---|
| Calculated % | 74.01 | 5.23 | 20.76 |
| Found % | 73.80 | 5.20 | 21.0 |

IR(KBr): 1,712 cm$^{-1}$ non-chelated C = O; 1,665 chelated C = O; 1,615 C = C; 1,595 ortho-disubstituted aromatic ring; 1,510 para-disubstituted aromatic ring; 1,240 ether bond.

NMR:

| | | | |
|---|---|---|---|
| CH$_3$ | 1.7 | ppm | doublet; |
| CH | 6.05 | ppm | quadruplet; |
| CH$_3$ | 2.2 | ppm | singlet; |
| OH | 11.8 | ppm | singlet. |

EXAMPLE 5

2.95 G (0.024 mol) of p-nitrophenol in 30 ml of toluene are added to a suspension of 2.5 g of sodium methylate in 25 ml of toluene. The mixture is stirred for 5 minutes and then 4.7 g (0.02 mol) of 2-(2'-chloropropionyl)indane-1,3-dione in 50 ml of toluene are introduced dropwise, followed by 20 ml of HMPT. The reaction mixture is refluxed for 17 hours and then, after cooling, is poured into aqueous hydrochloric acid and the resulting mixture is extracted with benzene. After exaporating the solvent, the residue is crystallised from ethanol to give 2 g of pure 2-[2'-(4''-nitrophenoxy)isopropionyl]indane-1,3-dione, melting point 145°C. Empirical formula: $C_{18}H_{13}O_6N$; molecular weight: 339.29; Elementary analysis:

| | C | H | N | O |
|---|---|---|---|---|
| Calculated % | 63.72 | 3.86 | 4.13 | 28.29 |
| Found % | 63.50 | 3.72 | 4.25 | 28.53 |

IR(KBr): 1,720 cm$^{-1}$ non-chelated C = O; 1,670 chelated C = O; 1,610 C = C; 1,600 ortho-disubstituted aromatic ring; 1,500 para-disubstitued aromatic ring; 1,240 ether bond; 1,350–1,515 NO$_2$.

| NMR: | CH₃ | 1.75 | ppm | doublet; |
|---|---|---|---|---|
| | CH | 6.75 | ppm | quadruplet; |
| | OH | 12.1 | ppm | singlet. |

EXAMPLE 6

3 G (0.024 mol) of p-methoxyphenol in 30 ml of toluene are added to a suspension of 2.5 g of sodium methylate in 25 ml of toluene; the mixture is stirred for 5 minutes and then 4.7 g (0.02 mol) of 2-(2'-chloropropionyl)indane-1,3-dione in 50 ml of toluene and 20 ml of HMPT are introduced dropwise. The mixture is refluxed for 17 hours and then, after cooling, is poured into aqueous hydrochloric acid and the resulting mixture is extracted with benzene. After evaporating the solvent, the residue is crystallised from isopropanol to give 5.1 g of pure 2-[2'-(4''-methoxyphenoxy)isopropionyl]indane-1,3-dione, melting point 74°C. Empirical formula: $C_{19}H_{16}O_5$; molecular weight: 324.32; Elementary analysis:

| | C | H | O |
|---|---|---|---|
| Calculated % | 70.36 | 4.98 | 24.66 |
| Found % | 70.55 | 5.22 | 24.23 |

IR(KBr): 1,715 cm⁻¹ non-chelated C = O; 1,670 chelated C = O; 1,615 C = C; 1,595 ortho-disubstituted aromatic ring.

| NMR: | CH₃ | 1.65 | ppm | doublet; |
|---|---|---|---|---|
| | CH | 6 | | quadruplet; |
| | CH₃ | 3.65 | ppm | singlet; |
| | 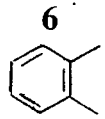 | 7.70 | | |
| | ⟨O⟩ | 6.8 | | |
| | OH | 12.55 | | singlet. |

EXAMPLE 7

3 G (0.024 mol) of ortho-chlorophenol in 30 ml of toluene are added to a suspension of 2.5 g of sodium methylate in 25 ml of toluene. After stirring the mixture for 5 minutes, 4.7 g (0.02 mol) of 2-(2'-chloropropionyl)indane-1,3-dione in 50 ml of toluene are introduced dropwise, followed by 20 ml of HMPT. The mixture is refluxed for 17 hours and then, after cooling, is poured into aqueous hydrochloric acid and the resulting mixture is extracted with benzene. After evaporating the solvent, the residue is crystallised from ethanol to give 1.3 g of pure 2-[2'-(2''-chlorophenoxy)isopropionyl]indane-1,3-dione, melting point 90-91°C. Empirical formula: $C_{18}H_{13}O_4Cl$; molecular weight: 328.76; Elementary analysis:

| | C | H | Cl | O |
|---|---|---|---|---|
| Calculated % | 65.76 | 3.99 | 10.78 | 19.47 |
| Found % | 65.60 | 4.25 | 10.67 | 19.68 |

IR(KBr): 1,715 cm⁻¹ non-chelated C = O; 1,675 chelated C = O; 1,615 C = C; 1,595 and 750

1,490 and 765

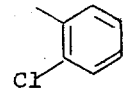

| NMR: | CH₃ | 1.73 | ppm | doublet; |
|---|---|---|---|---|
| | CH | 6.08 | ppm | quadruplet; |
| | —O—⟨⟩Cl | 7 | ppm | hump; |
| | ⟨⟩ | 7.70 | ppm | |
| | OH | 12.4 | ppm | singlet. |

EXAMPLE 8

3 G (0.024 mol) of meta-chlorophenol in 30 ml of toluene are added to a suspension of 2.5 g of sodium methylate in 25 ml of toluene. After stirring the mixture for 5 minutes, 4.7 g (0.02 mol) of 2-(2'-chloropropionyl)indane-1,3-dione in 50 ml of toluene are introduced dropwise, followed by 20 ml of HMPT. The mixture is refluxed for 17 hours and then, after cooling, is poured into aqueous hydrochloric acid and the resulting mixture is extracted with benzene. After evaporating the solvent, the residue is crystallised from isopropanol to give 5 g of pure 2-[2'-(3''-chlorophenoxy)isopropionyl]indane-1,3-dione, melting point 106°C. Empirical formula: $C_{18}H_{13}O_4Cl$; molecular weight: 328.76; Elementary analysis:

| | C | H | O | Cl |
|---|---|---|---|---|
| Calculated % | 65.76 | 3.99 | 19.47 | 10.78 |
| Found % | 65.85 | 4.15 | 18.95 | 11.05 |

IR(KBr): 1,715 cm⁻¹ non-chelated C = O; 1,660 chelated C = O; 1,620 C = C; 1,595 and 750

775

| NMR: | CH₃ | 1.7 | ppm | doublet; |
|---|---|---|---|---|
| | CH | 6.08 | ppm | quadruplet; |
| | ⟨⟩ | 7.75 | ppm; | |
| | OH | 12.05 | ppm | singlet. |

EXAMPLE 9

3 G (0.024 mol) or 3-trifluoromethyl-phenol in 30 ml of toluene are added to a suspension of 2.5 g of sodium methylate in 25 ml of toluene. After stirring the mixture for 5 minutes, 4.7 g (0.02 mol) of 2-(2'-chloropropionyl)indane-1,3-dione in 50 ml of toluene are introduced dropwise, followed by 20 ml of HMPT. The mixture is refluxed for 17 hours and then, after cooling, is poured into aqueous hydrochloric acid and the resulting mixture is extracted with benzene. After evaporating the solvent, the residue is crystallised from isopropanol to give 4.6 g of pure 2-[2'-(3''-trifluoromethylphenoxy)isopropionyl]indane-1,3-dione, melting point 91°C. Empirical formula: $C_{19}H_{13}O_4F_3$; molecular weight: 362.31; Elementary analysis:

|  | C | H | O | F |
|---|---|---|---|---|
| Calculated % | 62.98 | 3.62 | 17.67 | 15.73 |
| Found % | 62.70 | 3.80 | 18.05 | 15.55 |

IR(KBr): 1,720 cm$^{-1}$ non-chelated C = O; 1,665 chelated C = 0; 1,620 C = C; 1,595 and 750

1,500 and 800

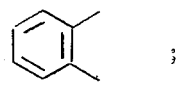

1,330, 1,170 and 1,130 CF$_3$; 1,220 ether bond

| NMR: | CH$_3$ | 1.75 | ppm | doublet; |
|---|---|---|---|---|
|  | CH | 6.15 | ppm | quadruplet; |

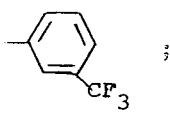

|  |  | 7.2 | ppm | hump; |
|---|---|---|---|---|
|  |  | 7.75 | ppm; |  |
|  | OH | 12.3 | ppm | singlet; |

EXAMPLE 10

3 G (0.024 mol) of phenol in 30 ml of toluene are added to a suspension of 2.5 g of sodium methylate in 25 ml of toluene. After stirring the mixture for 5 minutes, 4.7 g (0.02 mol) of 2-(2'-chloropropionyl)indane-1,3-dione dissolved in 50 ml of toluene are introduced dropwise, followed by 20 ml of HMPT. The mixture is heated under reflux for 17 hours and then after cooling, is poured into aqueous hydrochloric acid and the resulting mixture is extracted with benzene. After evaporating the solvent, the residue is crystallised from ethanol to give 1.3 g of pure 2-(2'-phenoxyisopropionyl)indane-1,3-dione, melting point 86° – 87°C. Empirical formula: $C_{18}H_{14}O_4$; molecular weight: 294.29; Elementary analysis:

|  | C | H | O |
|---|---|---|---|
| Calculated % | 73.46 | 4.80 | 21.75 |
| Found % | 73.30 | 4.90 | 21.80 |

IR(KBr): 1,715 cm$^{-1}$ non-chelated C = O; 1,670 chelated C = O; 1,605 C = C; 1,590 and 750

1,490 and 770-700

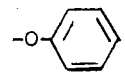

1,245 and 1,040

| NMR: | CH$_3$ | 1.70 | ppm | doublet; |
|---|---|---|---|---|
|  | CH | 6.1 | ppm | quadruplet; |
|  | OH | 12.5 | ppm | singlet. |

EXAMPLE 11

5.8 G of 2-(4-chlorophenoxy)butyryl chloride (0.025 mol) are added dropwise, with stirring and whilst cooling with an ice bath at 0°C and working under nitrogen, to 3.65 g (0.025 mol) of indane-1,3-dione in 20 ml of pyridine containing two drops of piperidine. After stirring the mixture for 18 hours, it is poured onto ice and acidified with hydrochloric acid, and the resulting mixture is ectracted with chloroform. After evaporating the solvent, the residue is crystallised from ethyl acetate to give 1.55 g of pure 2-[2'-(4''-chlorophenoxy)-butyryl]indane-1,3-dione, melting point 132°C. Empirical formula: $C_{19}H_{15}O_4Cl$; molecular Weight: 342.79; Elementary analysis:

|  | C | H | O | Cl |
|---|---|---|---|---|
| Calculated % | 66.57 | 4.42 | 18.67 | 10.34 |
| Found % | 66.20 | 4.68 | 18.67 | 10.45 |

IR(CHCl$_3$): 1,710 cm$^{-1}$ non-chelated C = O; 1,660 chelated C = O; 1,610 C = C; 1,595

1,490

1,240 ether bond.

| NMR: | CH$_3$ | 1.12 | ppm | triplet; |
|---|---|---|---|---|
|  | CH$_2$ | 2.05 | ppm | quintuplet; |
|  | CH | 5.84 | ppm | triplet; |
|  | OH | 12.35 | ppm | singlet. |

EXAMPLE 12

2.93 G (0.024 mol) of 3,4-dimethylphenol in 30 ml of toluene are added to a suspension of 2.5 g of sodium methylate in 25 ml of toluene. After stirring the mixture for 5 minutes, 4.7 g (0.02 mol) of 2-(2'-chloropropionyl)indane-1,3-dione in 50 ml of toluene are added dropwise, followed by 20 ml of HMPT. After the mixture has has been refluxed for 17 hours, it is poured into aqueous hydrochloric acid and the resulting mixture is extracted with benzene. Evaporation of the solvent and recrystallisation from ethanol gave 3.6 g of pure 2-[2'-(3'',4''-dimethylphenoxy)isopropionyl]-indane-1,3-dione, melting point 78°C. Empirical formula: $C_{20}H_{18}O_4$; molecular weight: 322.34; Elementary analysis:

|  | C | H | O |
|---|---|---|---|
| Calculated % | 74.52 | 5.63 | 19.85 |
| Found % | 74.10 | 5.80 | 20.10 |

IR(KBr): 1,715 $cm^{-1}$ non-chelated C = O; 1,665 chelated C = O; 1,615 C = C; 1,595 and 750

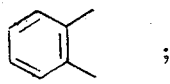

1,500 and 810

| NMR: | CH₃ | 1.70 ppm | doublet; |
|---|---|---|---|
|  | CH | 6.05 ppm | quadruplet; |
|  | Aromatic | 2.1 ppm |  |
|  | CH₃ | 2.13 ppm | singlets; |
|  | OH | 13 ppm | singlet. |

The anticoagulant activity of the compounds of the invention was measured in rats and rabbits, working on a homogeneous group of 3 to 9 animals.

The compounds are administered in the form of a mixture with maize starch, suspended in a mucilage of gum arabic.

Blood is removed from the anaesthetised animals and the plasma is used to measure the QUICK time, in accordance with the usual technique. A prior calibration, carried out on control plasma, makes it possible to evaluate the proportion of prothrombin and thus to draw, for a given dose, the graph of the decrease in the proportion of prothrombin with the passage of time.

This hypothrombinaemia-inducing effect characterises the anti-vitamin K activity of the compounds of the invention.

The graphs represented in FIGS. 1 to 15 of the attached Drawings give the proportion of prothrombin in %, plotted as the ordinates, as a function of the time at which the sample was removed, in hours, plotted as the abscissae. They illustrate the high hypothrombinaemia-inducing activity of these compounds, characterised by an active dose of approximately 0.1 mg/kg in the case of rabbits and 1 mg/kg in the case of rats.

FIG. 1 — anticoagulant activity of the compound of Example 1, in rats:
curve I: dose 1 mg/kg (9 rats per point);
curve II: dose 2 mg/kg (3 rats per point).

Figure 2:
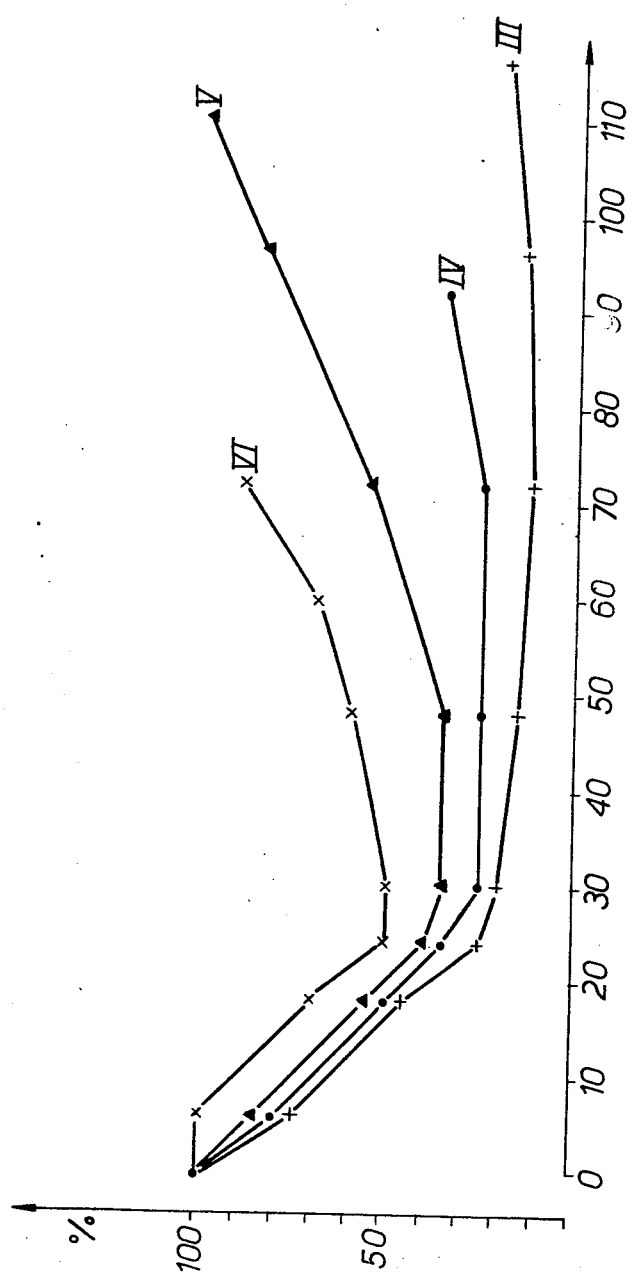

FIG. 2 — anticoagulant activity of the compound of Example 1, in rabbits:
curve III: dose 0.1 mg/kg (average of 8 experiments);
curve IV: dose 0.07 mg/kg (average of 4 experiments);
curve V: dose 0.06 mg/kg (average of 5 experiments);
curve VI: dose 0.05 mg/kg (average of 2 experiments).

Figure 3:
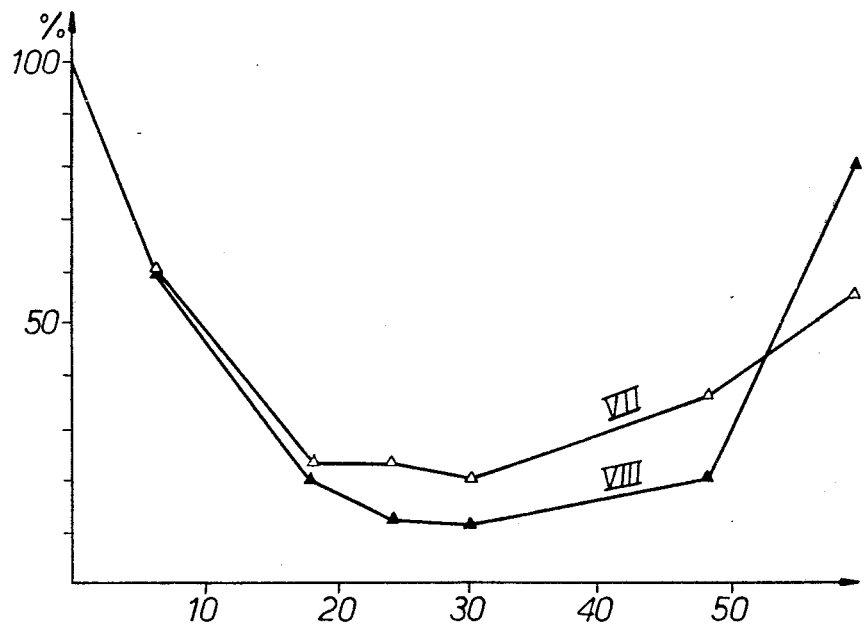

FIG. 3 — anticoagulant activity of the compound of Example 2, in rats:
curve VII: dose 1 mg/kg (6 rats per point);
curve VIII: dose 2 mg/kg (3 rats per point).

Figure 4:
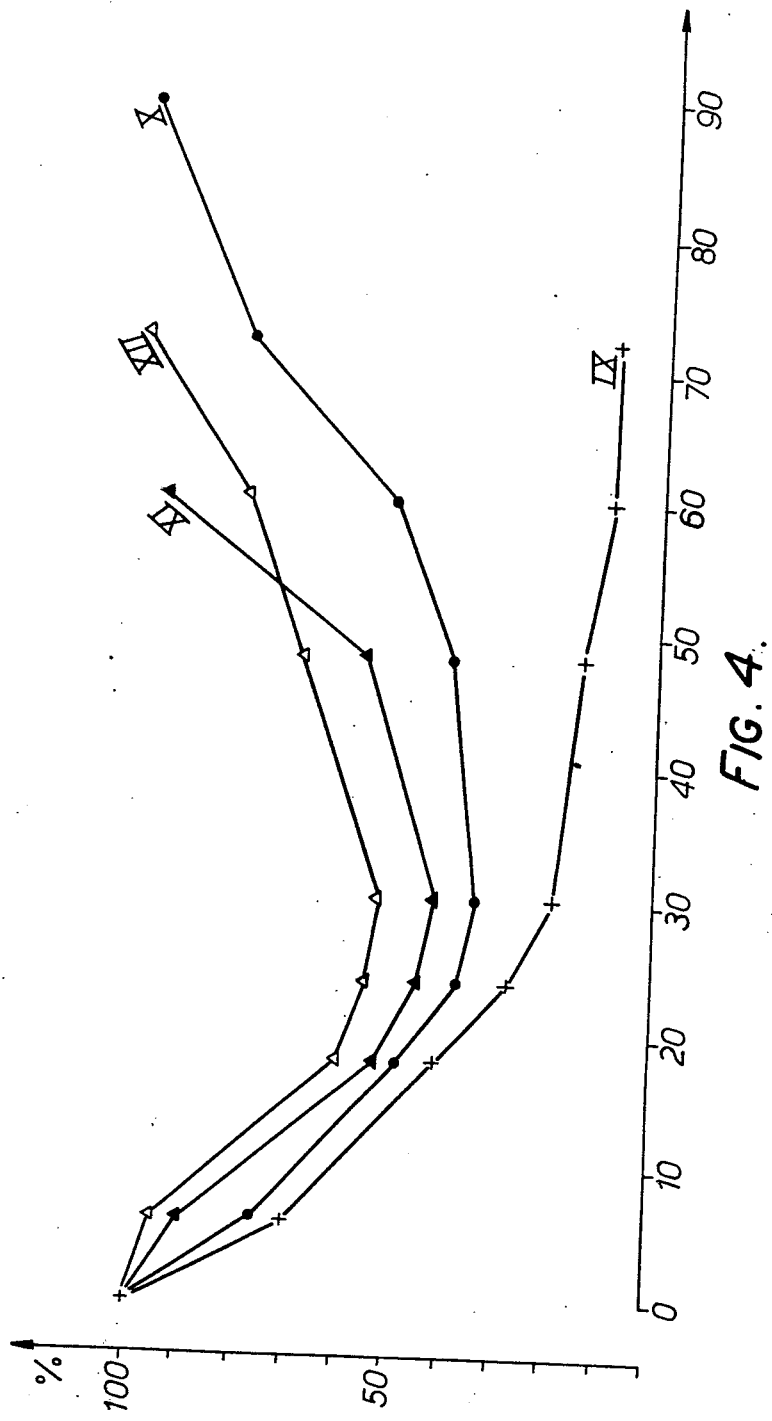

FIG. 4 — anticoagulant activity of the compound of Example 2, in rabbits:
curve IX: dose 0.1 mg/kg (average of 6 experiments)
curve X: dose 0.07 mg/kg (average of 8 experiments)
curve XI: dose 0.06 mg/kg (average of 2 experiments)
curve XII: dose 0.05 mg/kg (average of 2 experiments).

Figure 5:
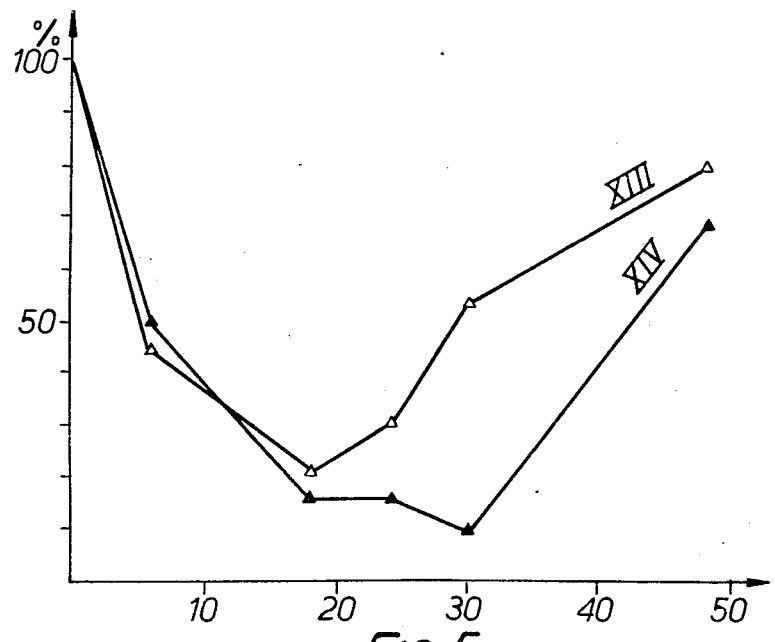

FIG. 5 — anticoagulant activity of the compound of Example 3, in rats:
curve XIII: dose 1 mg/kg (6 rats per point);
curve XIV: dose 2 mg/kg (3 rats per point)

Figure 6:
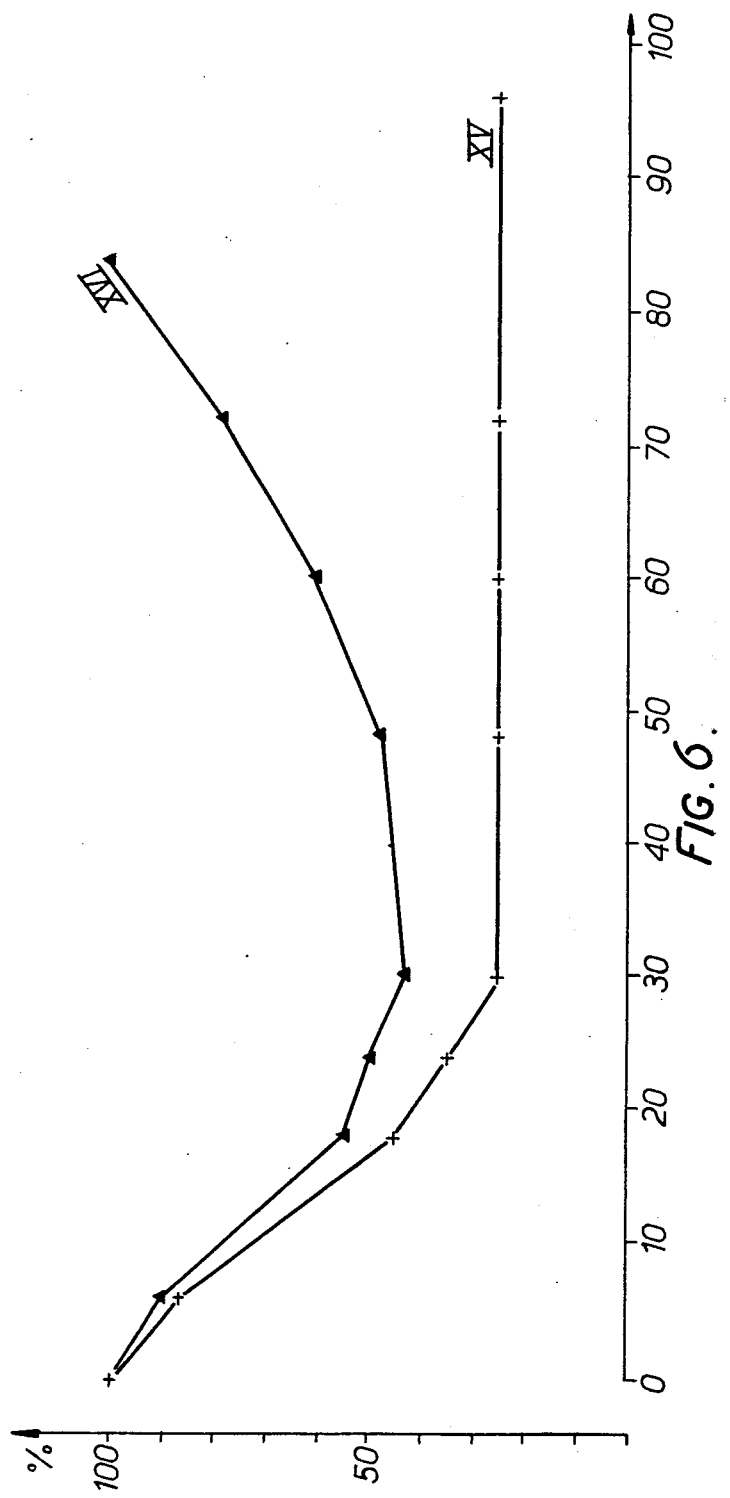

FIG. 6 — anticoagulant activity of the compound of Example 3, in rabbits:
curve XV: dose 0.1 mg/kg (average of 2 experiments);
curve XVI: dose 0.007 mg/kg (average of 3 experiments).

Figure 7:
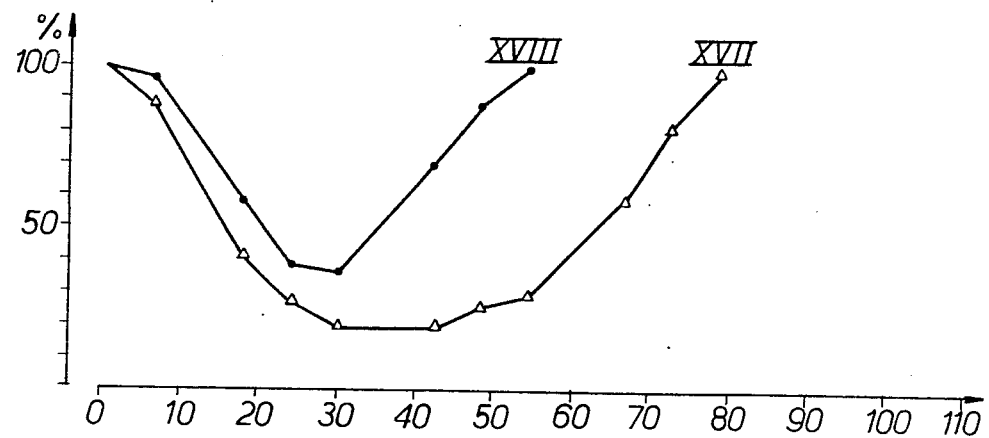

FIG. 7 — anticoagulant activity of the compound of Example 4, in rabbits:
curve XVII: dose 0.5 mg/kg (average of 5 experiments)
curve XVIII: dose 0.3 mg/kg (average of 4 experiments).

Figure 8:
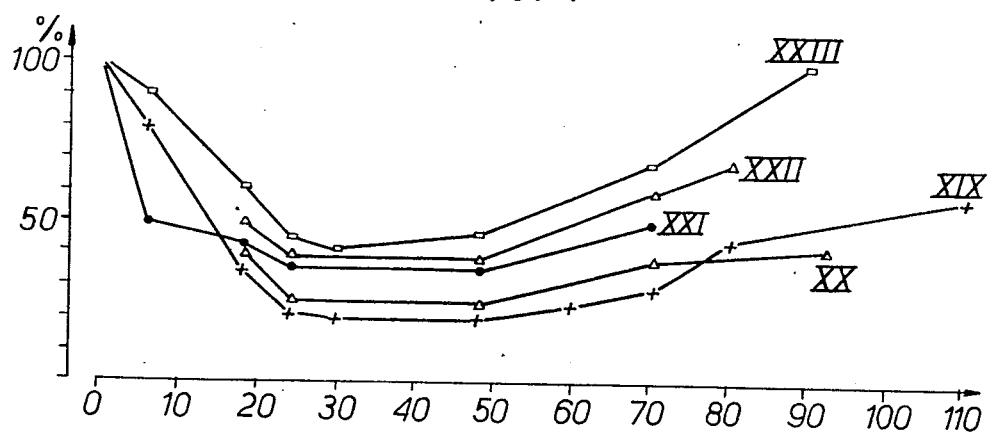

FIG. 8 — anticoagulant activity of the compound of Example 5, in rabbits:
curve XIX: dose 2 mg/kg (average of 5 experiments);
curve XX: dose 1.5 mg/kg (average of 2 experiments);
curve XXI: dose 1 mg/kg (3 experiments);
curve XXII: dose 0.5 mg/kg (3 experiments);
curve XXIII: dose 0.3 mg/kg (2 experiments).

Figure 9:
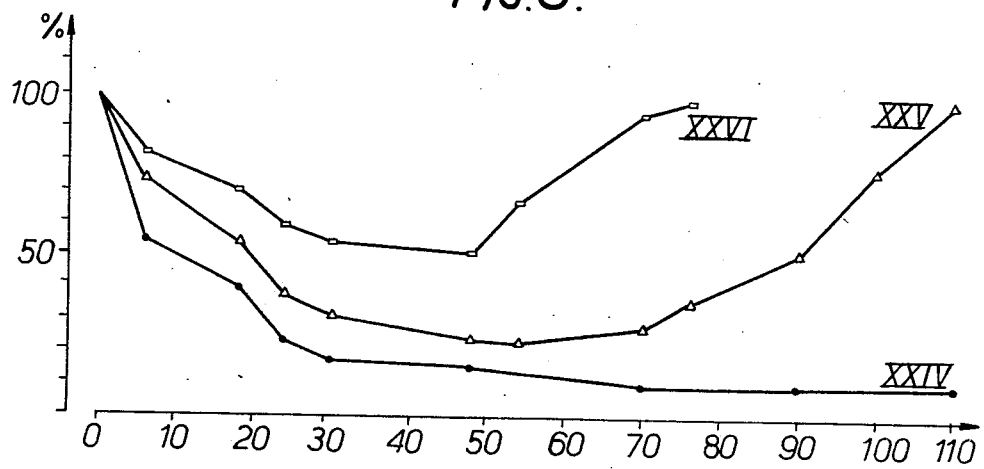

FIG. 9 — anticoagulant activity of the compound of Example 6, in rabbits:
curve XXIV: dose 1 mg/kg (3 experiments);
curve XXV: dose 0.5 mg/kg (5 experiments);
curve XXVI: dose 0.25 mg/kg (3 experiments).

Figure 10:
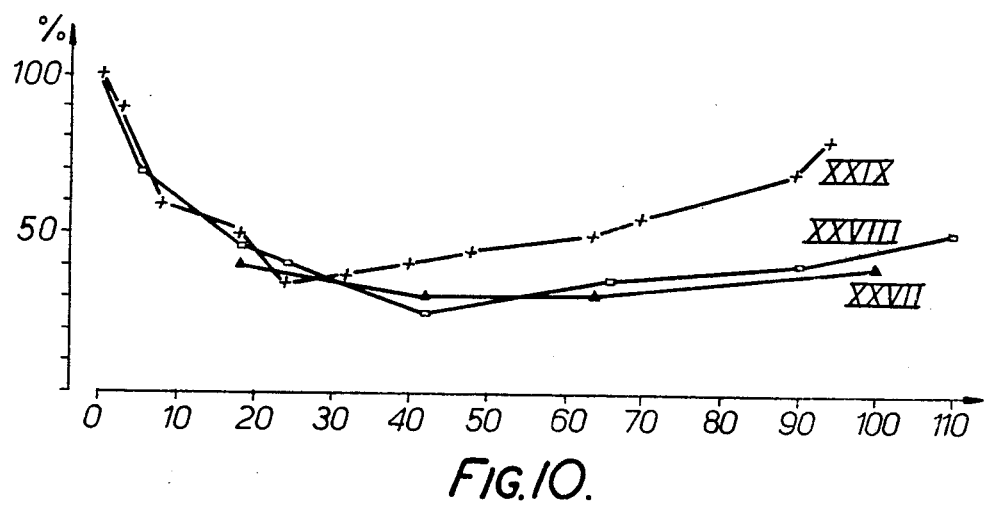

FIG. 10 — anticoagulant activity of the compound of Example 7, in rabbits:
curve XXVII: dose 0.05 mg/kg (2 experiments);
curve XXVIII: dose 0.3 mg/kg (3 experiments);
curve XXIX: dose 0.25 mg/kg (3 experiments).

Figure 11:
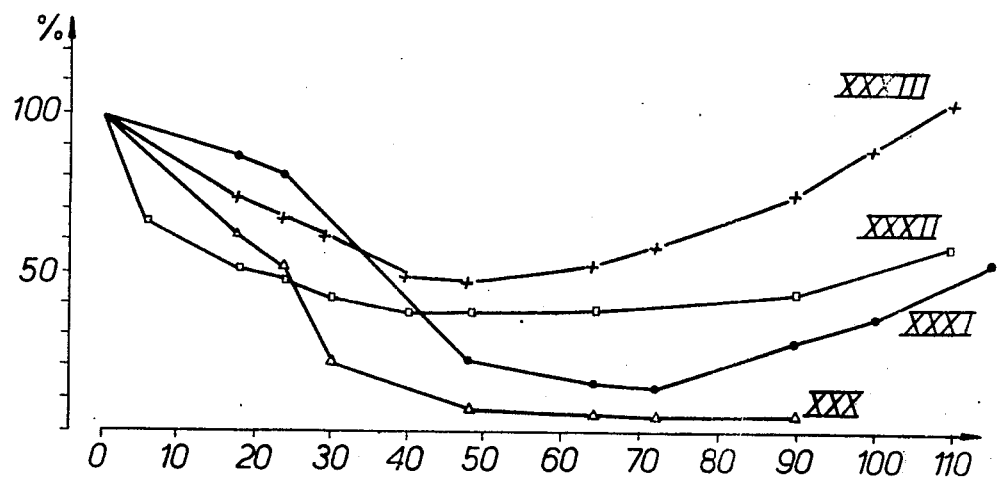

FIG. 11 — anticoagulant activity of the compound of Example 8, in rabbits:
curve XXX: dose 0.5 mg/kg (2 experiments);
curve XXXI: dose 0.25 mg/kg (2 experiments);
curve XXXII: dose 0.15 mg/kg (3 experiments);
curve XXXIII: dose 0.1 mg/kg (4 experiments).

Figure 12:
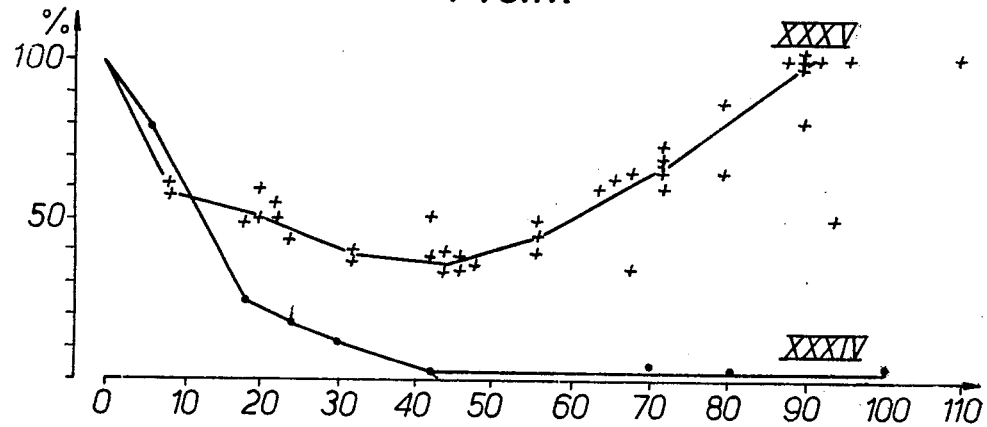

FIG. 12 — anticoagulant activity of the compound of Example 9, in rabbits:
curve XXXIV: dose 0.5 mg/kg (2 experiments);
curve XXXV: dose 0.05 mg/kg (5 experiments).

Figure 13:
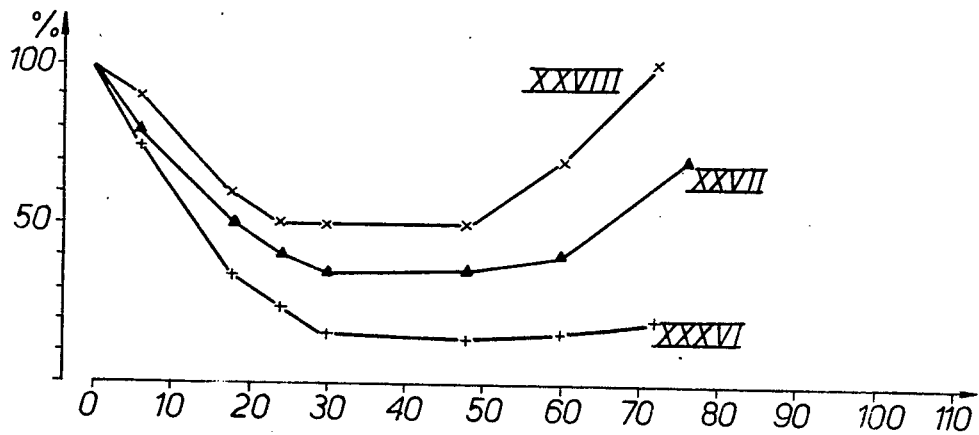

FIG. 13 — anticoagulant activity of the compound of Example 10, in rabbits:
curve XXXVI: dose 3 mg/kg (2 experiments)
curve XXXVII: dose 2 mg/kg
curve XXXVIII: dose 1.5 mg/kg.

Figure 14:
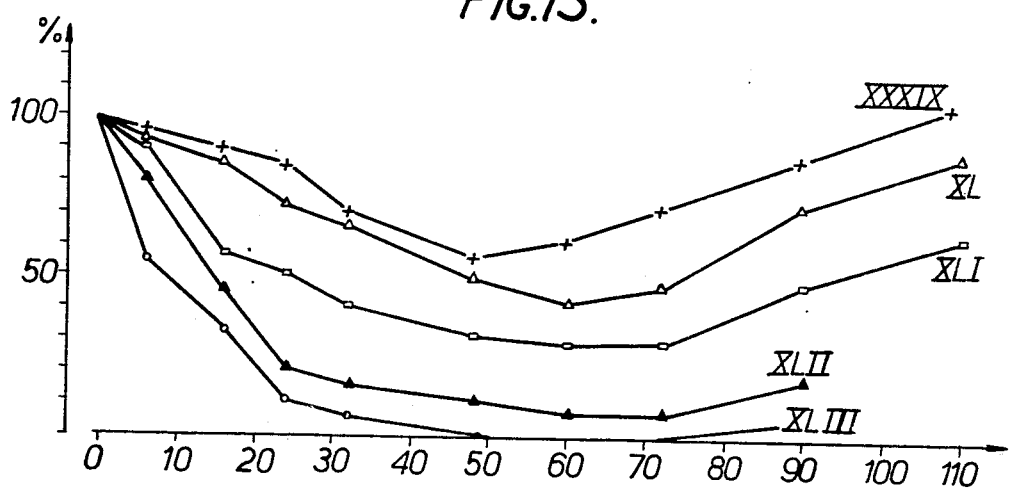

FIG. 14 — anticoagulant activity of the compound of Example 11, in rabbits:
curve XXXIX: dose 0.1 mg/kg;
curve XL: dose 0.2 mg/kg (4 experiments);
curve XLI: dose 0.25 mg/kg (2 experiments);
curve XLII: dose 0.3 mg/kg (2 experiments);
curve XLIII: dose 0.5 mg/kg (2 experiments).

Figure 15:
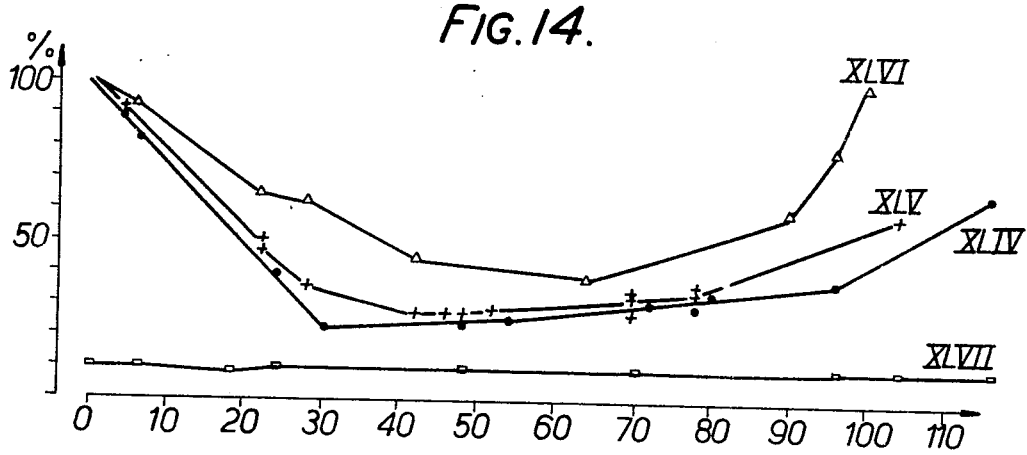

FIG. 15 — anticoagulant activity of the compound of Example 12, in rabbits:
curve XLIV: dose 0.5 mg/kg (3 experiments);
curve XLV: dose 0.3 mg/kg (3 experiments);
curve XLVI: dose 0.2 mg/kg (2 experiments).

In this Figure, the proportion of prothrombin is also given in curve XLVII as a function of the thrombin time in seconds (plotted as the abscissae).

The compounds of the invention possess powerful hypothrombinaemia-inducing activity and are useful in therapy as anticoagulants.

They can be made up in forms suitable for oral administration, for example in the form of tablets containing 2–10 mg of the active compound.

I claim:

1. A compound of general formula (I)

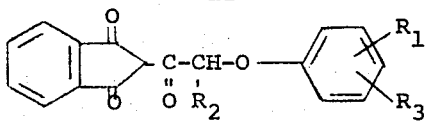

wherein each of the groups $R_1$ and $R_2$, which may be the same or different, is a hydrogen atom or an alkyl group having 1 to 3 carbon atoms and $R_3$ is a hydrogen or halogen atom, an alkyl group having 1 to 3 carbon atoms or a methoxy, trifluoromethyl or nitro group.

2. A compound as claimed in claim 1 which is 2-[2'-(4''-chlorophenoxy)isopropionyl]indane-1,3-dione.

3. A compound as claimed in claim 1 which is 2-[2'-(4''-bromophenoxy)isopropionyl]indane-1,3-dione.

4. A compound as claimed in claim 1 which is 2-[2°-(4''-fluorophenoxy)isopropionyl]indane-1,3-dione.

5. A compound as claimed in claim 1 which is 2-[2'-(4''-methylphenoxy)isopropionyl]indane-1,3-dione.

6. A compound as claimed in claim 1 which is 2-[2'-(4''-nitrophenoxy)isopropionyl]indane-1,3dione.

7. A compound as claimed in claim 1 which is 2-[2'-(4''-methoxyphenoxy)isopropionyl]indane-1,3-dione.

8. A compound as claimed in claim 1 which is 2-[2'-(2''-chlorophenoxy)isopropionyl]indane-1,3-dione.

9. A compound as claimed in claim 1 which is 2-[2'-(3''-chlorophenoxy)isopropionyl]indane-1,3-dione.

10. A compound as claimed in claim 1 which is 2-[2'-(3''-trifluoromethylphenoxy)isopropionyl]-indane-1,3-dione.

11. A compound as claimed in claim 1 which is 2-(2'-phenoxyisopropionyl)indane-1,3-dione.

12. A compound as claimed in claim 1 which is 2-[2'-(4''-chlorophenoxy)butyryl]indane-1,3-dione.

13. A compound as claimed in claim 1 which is 2-[2'-(3'',4''-dimethylphenoxy)isopropionyl]indane-1,3-dione.

* * * * *

UNITED STATES PATENT OFFICE
CERTIFICATE OF CORRECTION

Patent No. 3,957,879         Dated May 18, 1976

Inventor(s) Jean Mardiguian

It is certified that error appears in the above-identified patent and that said Letters Patent are hereby corrected as shown below:

Column 1, line 35, "$R_2$" (second occurrence) should read ---$R_3$---.

Column 4, line 56, "exaporating" should read ---evaporating---.

Signed and Sealed this

Ninth Day of November 1976

[SEAL]

Attest:

RUTH C. MASON
*Attesting Officer*

C. MARSHALL DANN
*Commissioner of Patents and Trademarks*